US007180585B2

United States Patent
Kreh et al.

(10) Patent No.: US 7,180,585 B2
(45) Date of Patent: Feb. 20, 2007

(54) APPARATUS FOR WAFER INSPECTION

(75) Inventors: Albert Kreh, Solms (DE); Henning Backhauss, Wetzlar (DE)

(73) Assignee: Leica Microsystems Semiconductor GmbH, Wetzlar (DE)

( * ) Notice: Subject to any disclaimer, the term of this patent is extended or adjusted under 35 U.S.C. 154(b) by 339 days.

(21) Appl. No.: 10/846,624

(22) Filed: May 17, 2004

(65) Prior Publication Data
US 2004/0239920 A1 Dec. 2, 2004

(30) Foreign Application Priority Data
May 30, 2003 (DE) ............... 103 24 474

(51) Int. Cl.
*G01N 21/00* (2006.01)
(52) U.S. Cl. ............... 356/237.2; 356/237.3; 356/237.4; 356/237.5
(58) Field of Classification Search .. 356/237.2–237.5, 356/367, 369
See application file for complete search history.

(56) References Cited
U.S. PATENT DOCUMENTS 4,850,711 A    7/1989  Sano et al.
6,630,995 B1 * 10/2003 Hunter .................... 356/237.5
6,771,374 B1 *  8/2004 Rangarajan et al. ........ 356/445
2003/0234927 A1 * 12/2003 Hunt ....................... 356/237.2
2004/0032581 A1 *  2/2004 Nikoonahad et al. .... 356/237.2

FOREIGN PATENT DOCUMENTS

DE    1 083 065       6/1960
DE    37 87 320 T2    12/1987
EP    0 647 827 B1    4/1995

OTHER PUBLICATIONS

I. Peterson et al., "Lithography Defects: Reducing and Managing Yield Killers through Photo Cell Monitoring", Yield Management Solutions, Spring 2000, pp. 17-24.

* cited by examiner

*Primary Examiner*—Layla G. Lauchman
*Assistant Examiner*—Tri Ton
(74) *Attorney, Agent, or Firm*—Foley & Lardner LLP

(57) ABSTRACT

An apparatus for wafer inspection is described, comprising an incident-light illumination device (5) having an illumination axis and an imaging device (9) having an image axis, both of which are inclined with respect to one another and are directed onto a region to be inspected of the surface (42) of a wafer (2). According to the present invention, the apparatus is characterized in that the incident-light illumination device (5) and the imaging device (9, 19) each have associated with them a polarizing means whose transmission axes are oriented at a predetermined angle to one another.

21 Claims, 6 Drawing Sheets

APPARATUS FOR WAFER INSPECTION

CROSS REFERENCE TO RELATED APPLICATIONS

This application claims priority of the German patent application 103 24 474.3 which is incorporated by reference herein.

FIELD OF THE INVENTION

The invention concerns an apparatus for wafer inspection.

BACKGROUND OF THE INVENTION

In semiconductor production, wafers are coated with photoresist during the production process. The photoresist passes first through an exposure process and then a development process. In these processes, it is patterned for subsequent process steps. For production-related reasons, slightly more photoresist becomes deposited in the edge region of the wafer than in the middle of the wafer. An "edge bead" is thereby formed. The photoresist at the edge of the wafer, and the edge bead, can lead to contamination of production machinery and to the creation of defects on the wafer in subsequent process steps.

To eliminate these effects, an edge bead removal (EBR) process is performed. Errors in the width of the edge bead removal derive from inaccurate alignment of the corresponding edge bead removal devices relative to the wafer. Inaccurate alignment of the illumination devices relative to the wafer upon exposure of the photoresist constitutes a further error source. Edge bead removal over too wide an edge region results in a decrease in the usable wafer area, and thus in a loss of chip production. Insufficient edge bead removal can result, in the edge region of the wafer, in contamination of the subsequently applied resist layers or other features. Incomplete bead removal in the edge region can also, upon handling of the wafer by means of handling tools which, for example, engage into the edge region of the wafer, lead to impurities, e.g. abraded material, which cause contamination of the rest of the wafer surface and diminished quality in downstream process steps. Since the productivity of the production process is diminished in such cases, edge bead removal (along with many other defects) must be continuously monitored during the production process. The edge bead removal width is monitored, and a check is made as to whether edge bead removal has in fact taken place.

Devices are known which, by image recognition, detect a wide variety of features on the surface of a wafer. In this context, the wafer is illuminated in bright-field fashion and scanned with a camera (matrix camera or linear camera).

One such inspection machine of KLA-Tencor Corporation is described in the article "Lithography Defects: Reducing and Managing Yield Killers Through Photo Cell Monitoring," by Ingrid Peterson, Gay Thompson, Tony DiBiase, and Scott Ashkenaz, Spring 2000, Yield Management Solutions. The wafer inspection device described therein operates with an incident-light illumination device that examines low-contrast microdefects using bright-field illumination.

EP 0 647 827 B 1 discloses a system for measuring the thickness of a thin-layer structure, in which light is irradiated onto the surface to be examined and interference rings are detected in the light reflected from the surface and evaluated using a computer, utilizing predefined learned patterns to determine the layer thickness.

In the known apparatuses for wafer inspection, the quality of the edge bead removal cannot easily be determined and assessed.

It is moreover difficult to make a distinction between the edge bead removal (EBR) and the other edges present in the image. These other edges derive from previous process steps. In bright-field illumination, all the edges are different in terms of color or grayscale value. Since the different edges also intersect or overlap in some cases, the color or grayscale value of the edges also changes. It is therefore very difficult or impossible to filter out the edge bead removal in this fashion using an image processing system. Even a visual inspection by an observer produces no better results, since the human eye also cannot manage to allocate the various edges and observed colors or grayscale values to the various process steps.

SUMMARY OF THE INVENTION

It is therefore the object of the present invention to describe an apparatus with which regions from which resist has been removed, in particular edge-bead-removed regions, can reliably be made visible and the quality of the edge bead removal can easily be determined or assessed.

This object is achieved by way of an apparatus for wafer inspection comprising an incident-light illumination device having an illumination axis, an imaging device having an image axis, wherein the both illumination axis and the image axis are inclined with respect to one another and are directed onto a region on a surface of a wafer to be inspected, and a polarizing means is associated with each of the incident-light illumination device and the imaging device, wherein transmission axes of the polarizing means are oriented at a predetermined angle to one another.

The above object is achieved as well by an apparatus for wafer inspection, comprising an incident-light illumination device having an illumination axis, an imaging device having an image axis, wherein the both illumination axis and the image axis are inclined with respect to one another and are directed onto a region on a surface of a wafer, wherein the region to be inspected is located on a wafer edge, a polarizing means associated with each of the incident-light illumination device and the imaging device, wherein transmission axes of the polarizing means are oriented at a predetermined angle to one another, and a wafer underside illumination device is arranged below the wafer edge, which illuminates the imaging device from below beyond the wafer edge.

The object is as well achieved by an apparatus for wafer inspection, comprising an incident-light illumination device having an illumination axis, an imaging device having an image axis, wherein the both illumination axis and the image axis are inclined with respect to one another and are directed onto a region on a surface of a wafer, wherein the region to be inspected is located on a wafer edge, a polarizing means associated with each of the incident-light illumination device and the imaging device, wherein transmission axes of the polarizing means are oriented at a predetermined angle to one another, a wafer underside illumination device is arranged below the wafer edge, which illuminates the imaging device from below beyond the wafer edge, a receiving device rotatable about its vertical axis is provided for placement of the wafer; a motorized drive system rotates the receiving device is associated with the receiving device, and a data readout device being associated with a camera, wherein the data readout device sequentially reads out the image data of the camera during the rotary motion of the wafer; and the data readout device is also associated with a computer that controls the data readout device.

The first polarizing means polarizes the light emitted by the incident-light illumination device in a polarization direction predefined by its transmission axis. The illuminating light polarized in this fashion strikes the surface of the wafer to be inspected, and is reflected there at treated and/or untreated surface regions. The polarization of the light is modified to different extents upon reflection at untreated surface regions and treated surface regions of the wafer. The light thus reflected arrives at the polarizing means associated with the imaging device, and is analyzed by it. The two polarizing means are designed so that they respectively allow the passage of light in a substantially mutually orthogonal polarization state.

Behind the polarizing means associated with the imaging device, there is therefore a distinction between the intensity of light components reflected from untreated surface regions of the wafer and the intensity of light components reflected from treated surface regions of the wafer. The imaging device receives the different signal components and conveys them to a further evaluation unit with which the untreated and treated surface regions of the wafer can be distinguished from one another and can be assessed in terms of the quality of the surface treatment, for example the edge bead removal.

The untreated surface regions are surface regions that have not yet been subjected to the process step that is to be assessed, whereas the treated surface regions of the wafer are those surface regions that have already been subjected to the process step that is to be assessed. The process step is preferably an edge bead removal, implemented e.g. by selective spraying of a solvent onto edge regions of a wafer and subsequent rinsing off of the solvent and the dissolved photoresist. Other edge bead removal techniques are, in principle, also possible. Other process steps, for example exposure, tempering, metallization, etc, are also eligible, in principle, as treatments whose quality and influence on selected surface regions of the wafer is to be assessed according to the present invention. Inspection of the wafer can also be performed continuously during the process step, for example on surface regions that are arranged at a distance from a treatment volume just processed, i.e. that have, for example, been rotated away from the region where the solvent that dissolves the photoresist is sprayed. Partially treated surface regions, for example partially edge-bead-removed regions, can of course also be determined and assessed as to their quality.

Although edge regions of the wafer are preferably inspected, according to the present invention any other desired regions on the surface of a wafer or semiconductor substrate can also, in principle, also be inspected, for which purpose the illuminating light is directed appropriately onto the region to be inspected, and the light reflected there is imaged appropriately into the imaging device. For imaging of the illuminating light and of the light reflected from the surface, further imaging means, for example deflecting mirrors, prisms, or the like, can be introduced into the beam path so that the apparatus can be configured in even more variable fashion.

The respective polarizing means is associated with the incident-light illumination device or with the imaging device by arranging it in the respective beam path at a suitable location. In particularly preferred fashion, the polarizing means is arranged directly in front of the associated incident-light illumination device or the imaging device, for example it is held and, in even more preferred fashion, directly joined thereto.

Each polarizing means is preferably characterized by a respective transmission axis. Light that passes through the respective polarizing means is linearly polarized along the respective transmission axis. Preferably, at least one of the polarizing means is rotatably mounted in order to modify the relative orientation of the transmission axes, for example in order to perform a zero balance or intensity balance.

The transmission axes of the two polarizing means are preferably aligned relative to one another so that an optimum contrast between treated and untreated surface regions of the wafer can be achieved. For this purpose, the transmission axes are preferably coordinated with one another, using light that is reflected exclusively from untreated or treated surface regions of the wafer, in such a way that the light behind the polarizing means associated with the imaging device substantially disappears (zero balancing). This has the advantage that the gain of the imaging device can be set relatively high, so that even very small intensity changes, brought about by changes in the polarization state of the light reflected at surface regions having differing properties, will result in relatively large signal amplitudes. The aforesaid zero balancing is preferably performed on the basis of the surface regions that predominate in terms of area. For example, if a comparatively small edge-bead-removed region is to be determined and assessed, the aforesaid zero balancing operation is preferably performed on the basis of regions from which no resist has been removed.

It is particularly preferred if the transmission axes of the two polarizing means are substantially perpendicular to one another, so as to constitute a pair made up of polarizer and crossed analyzer. The transmission axis of the polarizing means associated with the incident-light illumination device is preferably aligned perpendicular to the incidence plane extending between the illumination axis and the image axis, so that the light incident on the wafer surface to be inspected is polarized perpendicular to the incidence plane. The polarizing means associated with the imaging device is then aligned so as to perform the aforesaid zero balancing preferably on untreated surface regions, for example those from which resist has not been removed. Satisfactory results can, however, also be achieved according to the present invention with a different alignment of the transmission axes.

The illumination axis is preferably inclined at an illumination angle other than zero with respect to a wafer normal line through the incidence point. The image axis is also preferably arranged inclined at an image angle other than zero with respect to the wafer normal line through the incidence point. In this case the best imaging properties are obtained if the image angle $\beta$ is equal to the illumination angle $\alpha$, so that in this embodiment of the apparatus, the illumination angle $\alpha$ is defined by the inclination of the illumination axis with respect to the wafer normal line through the incidence point.

According to a first preferred embodiment, the illumination angle $\alpha$ corresponds to the Brewster angle of the material of the wafer to be inspected, for example silicon, or of a layer applied onto the wafer to be inspected, for example a photoresist layer that is to be removed from the edge region. In this case the light reflected from the material or from the layer applied thereto is reflected in such a way that it is polarized perpendicular to the image plane extending between the illumination axis and image axis. The aforementioned zero balancing can thus easily be performed by simply rotating the polarizing means associated with the imaging device, so that its transmission axis lies in the image plane. Although the term "zero balancing" is used hereinafter, it should be noted that this can also be incomplete, as a result in particular of inhomogeneities and irregularities on the surface of the wafer to be inspected. In order to perform the aforementioned zero balancing, it may also be advantageous if the illumination angle α does not correspond exactly to the Brewster angle, but instead is inclined at a preferably small angle toward or away from the wafer normal line. This makes it possible, for example, to compensate for inhomogeneities and irregularities on the surface of the wafer to be inspected.

According to a further preferred embodiment, the illumination angle α is relatively small, so that the illuminating light is incident at a relatively steep angle onto the surface to be inspected. The illumination angle α is preferably in the range from approximately 7 degrees to approximately 20 degrees, preferably in the range from approximately 14 degrees to approximately 16 degrees in order to produce even more advantageous properties for zero balancing, and in even more preferred fashion it is approximately 15 degrees in order to achieve even more advantageous zero balancing properties. This takes into account the effect that thin, relatively regular features, for example conductor paths, circuit features, etc, that are often provided on the wafer surface act like a groove grating, thus resulting in diffraction effects and polarization effects. These can have an influence on the aforementioned zero balancing, which can be compensated for by setting the illumination angle to a relatively steep incidence angle. In principle, a stepless transition between the aforementioned Brewster angle and the relatively steep incidence angle just mentioned is possible for illumination angle α.

The illumination device can be equipped both with a polychromatic and with a monochromatic light source. For example, the light source can be a mercury vapor lamp or a cold light source having an attached fiber bundle for transmitting the light. The use of an LED or a laser with beam spreading is also conceivable. Both a divergent and a convergent illumination beam path are usable. In a preferred embodiment, a telecentric illumination beam path is preferred, slight deviations from strictly telecentric beam guidance being permissible with no loss of illumination quality.

The imaging device usually comprises an objective and a camera or linear camera arranged thereafter, onto which the region to be inspected is imaged. Differently sized regions can therefore be inspected using the camera image, depending on the linear magnification defined by the objective.

An imaging device that encompasses an objective and a linear camera is preferably used for the inspection of wafer defects and areas in the region of the wafer edge from which resist has been removed.

Alignment marks on the wafer, or salient edge features such as the so-called flat or notch, can be used as the reference point for localizing observed defects and edge-bead-removed regions. For simplification, however, the wafer edge itself is preferably used. To make that wafer edge more visible, in a particularly advantageous embodiment of the apparatus a wafer underside illumination device is additionally provided, positioned beneath the wafer in the region of the wafer edge. This wafer underside illumination device radiates from below beyond the wafer edge and illuminates the imaging device. A definite light/dark transition, which exactly reproduces the wafer edge, is thereby made visible in the camera image or the linear camera.

To allow an inspection of the entire wafer edge to be performed, the wafer is preferably placed onto a receiving device that is rotatable about its center. For automated inspection of the wafer edge, this receiving device is coupled to a motorized drive system that performs a precise rotation of the receiving device. For automatic inspection of the edge region of the wafer, the apparatus has associated with it a data readout device which sequentially reads out the image data of the linear camera during the rotary motion of the wafer on the receiving device. A computer connected to the apparatus controls the motorized drive system and the data readout device. Alternatively, an encoder is provided that triggers the camera and/or the data readout device (e.g. frame grabber).

From the image data acquired sequentially during rotation of the wafer, various parameters or defects can then be determined using the computer. For example, the location on the wafer edge of the so-called wafer flat, or the location of the so-called wafer notch, can be determined.

To determine the location and quality of the edge bead removal (EBR) on the wafer, the wafer is rotated through 360° at least once. The image data sequentially acquired during this rotation are evaluated, in which context the high-contrast light-dark transition or dark-light transition identifies the location of the EBR edge. From the location of the EBR edge relative to the wafer edge, which is made visible by the wafer underside illumination device, the extent of the edge bead removal, or its deviations from target values relative to the wafer edge, can be determined.

BRIEF DESCRIPTION OF THE DRAWINGS

The invention will be explained below by way of example and with reference to the attached Figures, in which identical reference characters designate identical or substantially identically functioning elements and in which.

DETAILED DESCRIPTION OF THE INVENTION

Figure 1:
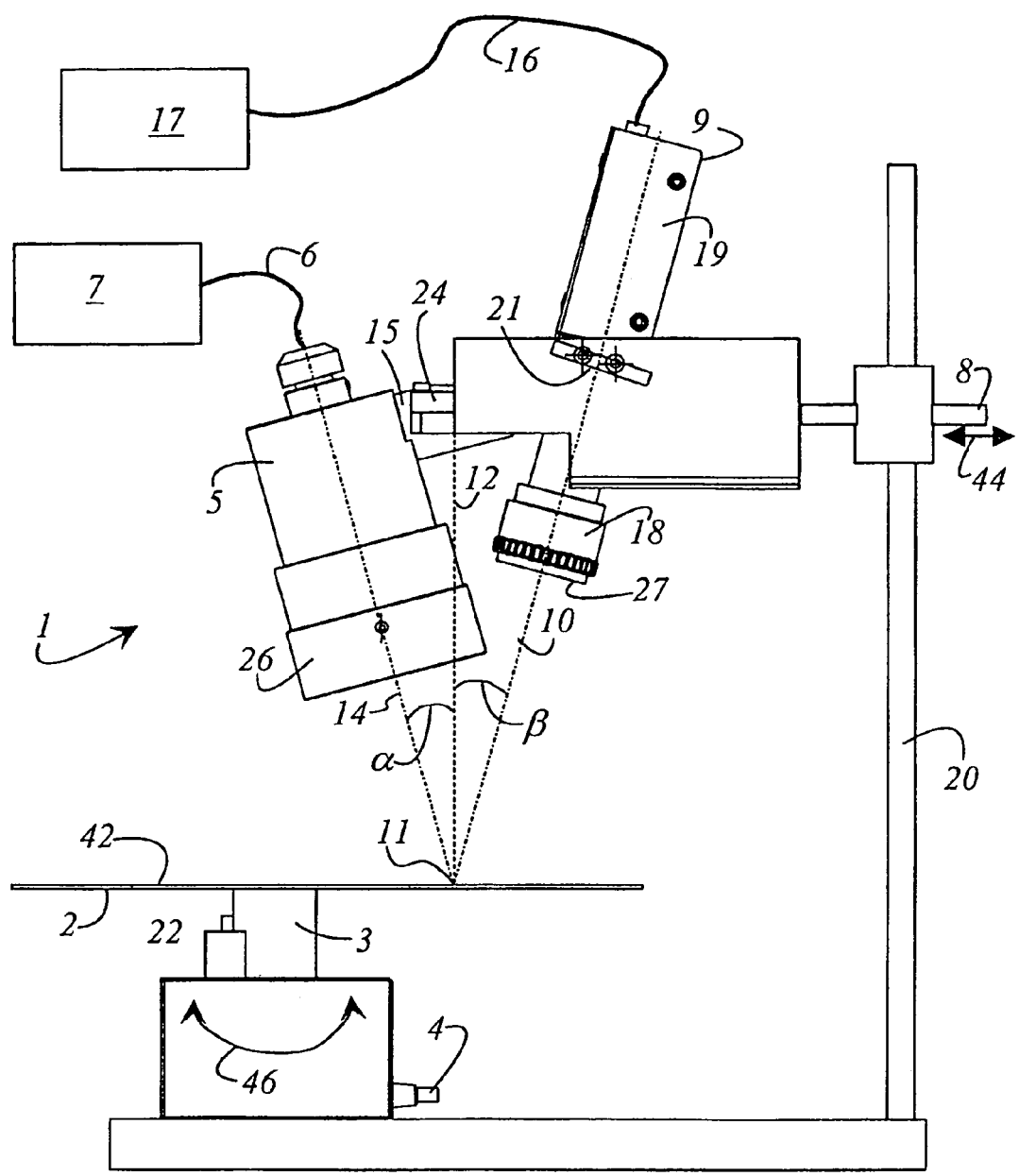
FIG. 1 is a side view of an apparatus for wafer inspection of the wafer edge or edge-bead-removal region, according to the present invention.

FIG. 1 shows an apparatus 1 for wafer inspection with a wafer 2 to be inspected. Wafer 2 is placed onto a receiving device 3 that retains wafer 2 by vacuum suction. The necessary vacuum is conveyed to receiving device 3 by means of a vacuum line 4 that is connected to a vacuum system (not depicted) for generating the vacuum.

An incident-light illumination device 5, to which light is conveyed from a light source 7 via a light-guide bundle 6, is directed onto a region to be inspected of wafer 2. Incident-light illumination device 5 is arranged at an inclination with respect to surface 42 of wafer 2. An imaging device 9 is arranged on a longitudinally displaceable support element 8. The direction of the longitudinal displacement is indicated by double arrow 44. Imaging device 9 has an image axis 10. Defined at incidence point 11 of this image axis 10 on wafer 2 is a wafer normal line 12, i.e. a construction line that is perpendicular to wafer 2 at incidence point 11. In the depiction, wafer normal line 12 intersects surface 42 of wafer 2 at incidence point 11.

In the embodiment depicted of apparatus 1 for wafer inspection, image axis 10 is inclined at an image angle β with respect to wafer normal line 12, i.e. imaging device 9 is arranged at an inclination with respect to the surface of wafer 2. As a result, there extends between image axis 10 and wafer normal line 12 an image plane that is preferably perpendicular to the wafer surface. The image plane can deviate by +/−15° from the vertical position.

Incident-light illumination device 5 has an illumination axis 14 that is inclined at illumination angle α with respect to wafer normal line 12. In the embodiment depicted of apparatus 1 for wafer inspection, illumination axis 14 strikes wafer 2 at incidence point 11, i.e. at the same location at which image axis 10 also strikes wafer 2. In the present case, therefore, illumination angle α is defined as the inclination of illumination axis 14 with respect to wafer normal line 12. Adjustment of the illumination angle α is accomplished by means of the α-adjustment device, which is embodied as alignment rail 24 and on which incident-light illumination device 5 is mounted. It proves to be advantageous if image angle β is identical to illumination angle α. A good image is still obtained, however, even if illumination angle α and image angle β are slightly different.

To allow different regions of wafer 2 to be inspected, imaging device 9 is displaceable by displacement of support element 8 over surface 42 of wafer 2. Since imaging device 9 and illumination device 5 are rigidly joined to one another via a common adjustable support bar 15, displacement of support element 8 causes the entire apparatus 1 to be displaced over the surface of wafer 2 to the desired region to be inspected. To make it easier to find any desired regions of the surface of wafer 2 that are to be inspected, wafer 2 is additionally mounted rotatably on receiving device 3. The rotary motion is indicated symbolically by a curved double arrow 46. Usually wafer 2 is held firmly in place on receiving device 3 by vacuum suction, and receiving device 3 itself is embodied rotatably.

By suitable displacement of support element 8, incident-light illumination device 5 and imaging device 9 can thus be displaced together, and any desired regions that are to be inspected on wafer 2 can be examined. The image data acquired in each case by imaging device 9, which comprises e.g. an objective 18 and a camera 19, are transferred via a data line 16 to a data readout device 17 or a computer.

As may be inferred from FIG. 1, a polarizer 26 serving as polarizing means, which preferably is rotatably mounted and directly attached, is placed onto the front end of incident-light illumination device 5. A polarizer 27 serving as polarizing means, which preferably is rotatably mounted and directly attached, is furthermore placed onto the front end of imaging device 9 and of objective 18. Polarizer 27 is used as the analyzer to analyze the polarization state of the light reflected, in the region of incidence point 11, from surface 42 of wafer 2.

Figure 2:
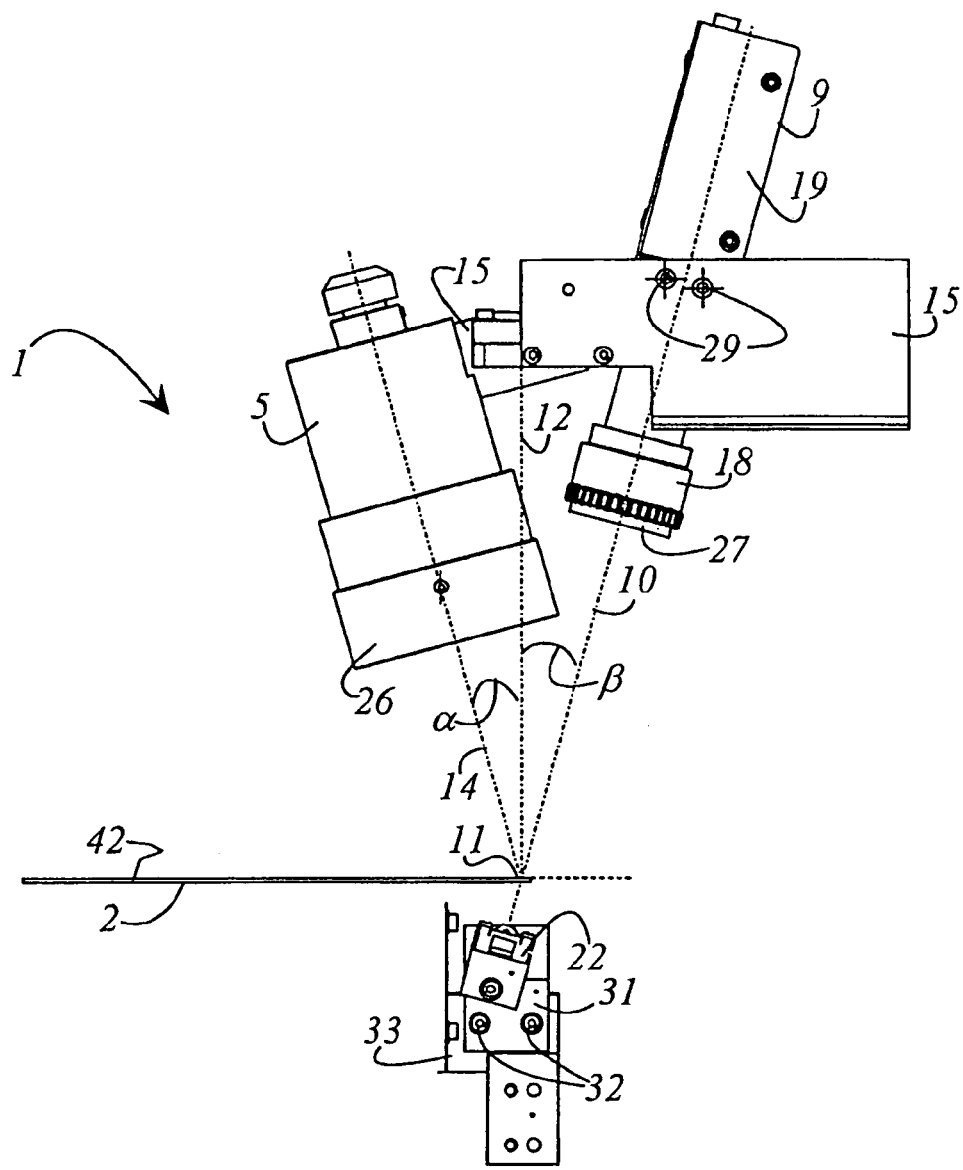
FIG. 2 is an enlarged side view depicting the illumination device and the imaging device according to FIG. 1.

FIG. 2 shows, in an enlarged side view, the arrangement of incident-light illumination device 5 and imaging device 9 according to FIG. 1. It is apparent from the upper part of FIG. 2 that imaging device 9, which encompasses a camera 19 and objective 18, is attached to support bar 15 with the aid of attachment screws 29 that serve as securing means. The inclination of imaging device 9 and camera 19 relative to support bar 15 can be modified by loosening attachment screws 29. As may be inferred from FIG. 1, image angle β can be modified by pivoting imaging device 9 along the curved alignment rail 21 that serves as the α-adjustment device.

Arranged below incidence point 11 is wafer underside illumination device 22, whose center point lies on image axis 10 and which is oriented so that light that is emitted from wafer underside illumination device 22 enters imaging device 9 collinearly with image axis 10. If applicable, an imaging optical system, for example a deflecting mirror, lens, or objective, can be arranged between wafer underside illumination device 22 and wafer 2.

As may be inferred from FIG. 2, wafer underside illumination device 22 is attached pivotably to an attachment block 31. The inclination of wafer underside illumination device 22 is modifiable, and in the exemplary embodiment depicted can be modified by loosening attachment screws 32 that serve as securing means, and tightening them again after suitably orienting wafer underside illumination device 22. Attachment block 31 is attached to a translation step 33 that can be displaced along the radial direction of wafer 2 or also along two mutually orthogonal displacement axes parallel to surface 42 of the wafer. Wafer underside illumination device 22 can thus be moved even over long distances so as to ensure, even in the case of a comparatively large change in image angle β, that the light emitted from wafer underside illumination device 22 is imaged into imaging device 9.

In FIG. 1, where it is depicted perpendicular to the drawing plane, wafer underside illumination device 22 is thus pivotable perpendicular to the drawing plane. Wafer underside illumination device 22 can furthermore be displaced in FIG. 1 in the radial direction of wafer 2, i.e. linearly in the drawing plane of FIG. 1.

Figure 3:
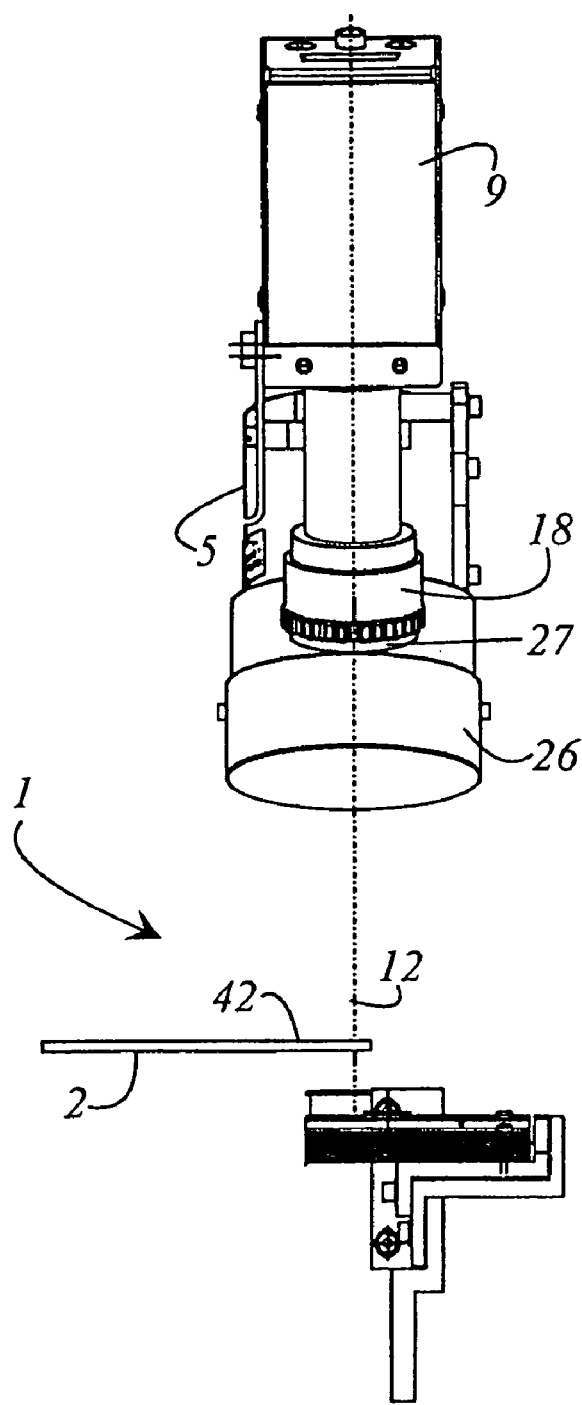
FIG. 3 depicts the arrangement of FIG. 2 rotated 90 degrees.

FIG. 3 shows the arrangement according to FIG. 2 in a view rotated 90 degrees. As depicted, incident-light illumination device 5 has an attached polarizer 26.

Figure 4:
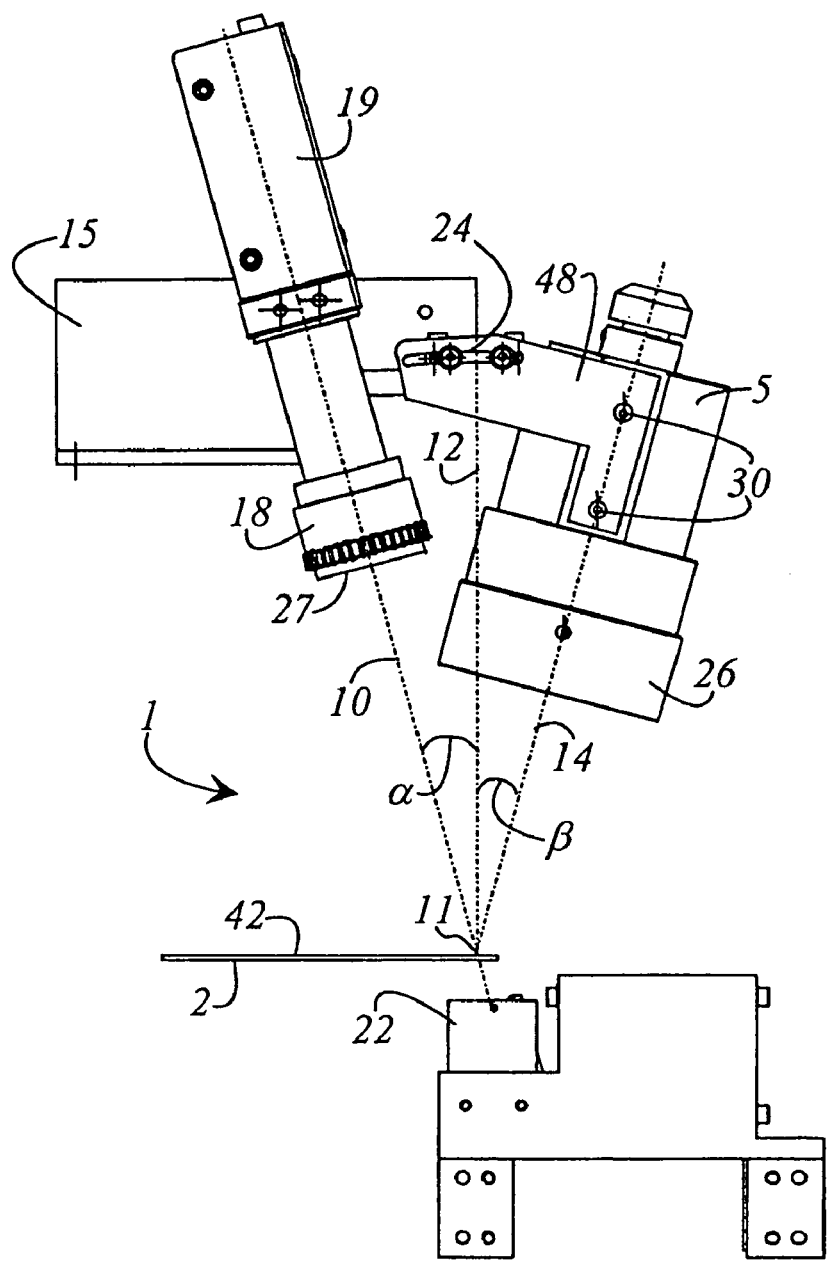
FIG. 4 depicts the arrangement of FIG. 3 from an opposite side.

FIG. 4 shows the arrangement according to FIG. 2 as viewed from the rear. As depicted, an L-shaped attachment arm, to which incident-light illumination device 5 is attached, is attached to support bar 15 by way of the curved alignment rail 24 serving as the α-adjustment device. Illumination device 5 and imaging device 9 are thus retained together. Once the apparatus is aligned, reliable operation can thus be guaranteed.

Illumination device 5 and imaging device 9 can, of course, also be mounted on separate support elements.

As depicted in the top part of FIG. 4, incident-light illumination device 5 is attached to an L-shaped element 48. Attachment elements 30 hold incident-light illumination device 5 on an L-shaped element 48. The radius of alignment rail 24 is preferably coordinated with the distance between incident-light illumination device 5 and incidence point 11 in such a way that the location of incidence point 11 on surface 42 of wafer 2 does not change substantially as pivoting occurs and illumination angle α changes. In the same fashion, the radius of alignment rail 21 (see FIG. 1) serving as the α-adjustment device is preferably also coordinated with the distance between imaging device 9 and incidence point 11. The image angle β is thus modified as imaging device 9 is pivoted along alignment rail 21, and the location of incidence point 11 on surface 42 of wafer 2 remains substantially stationary upon pivoting.

Figure 5:
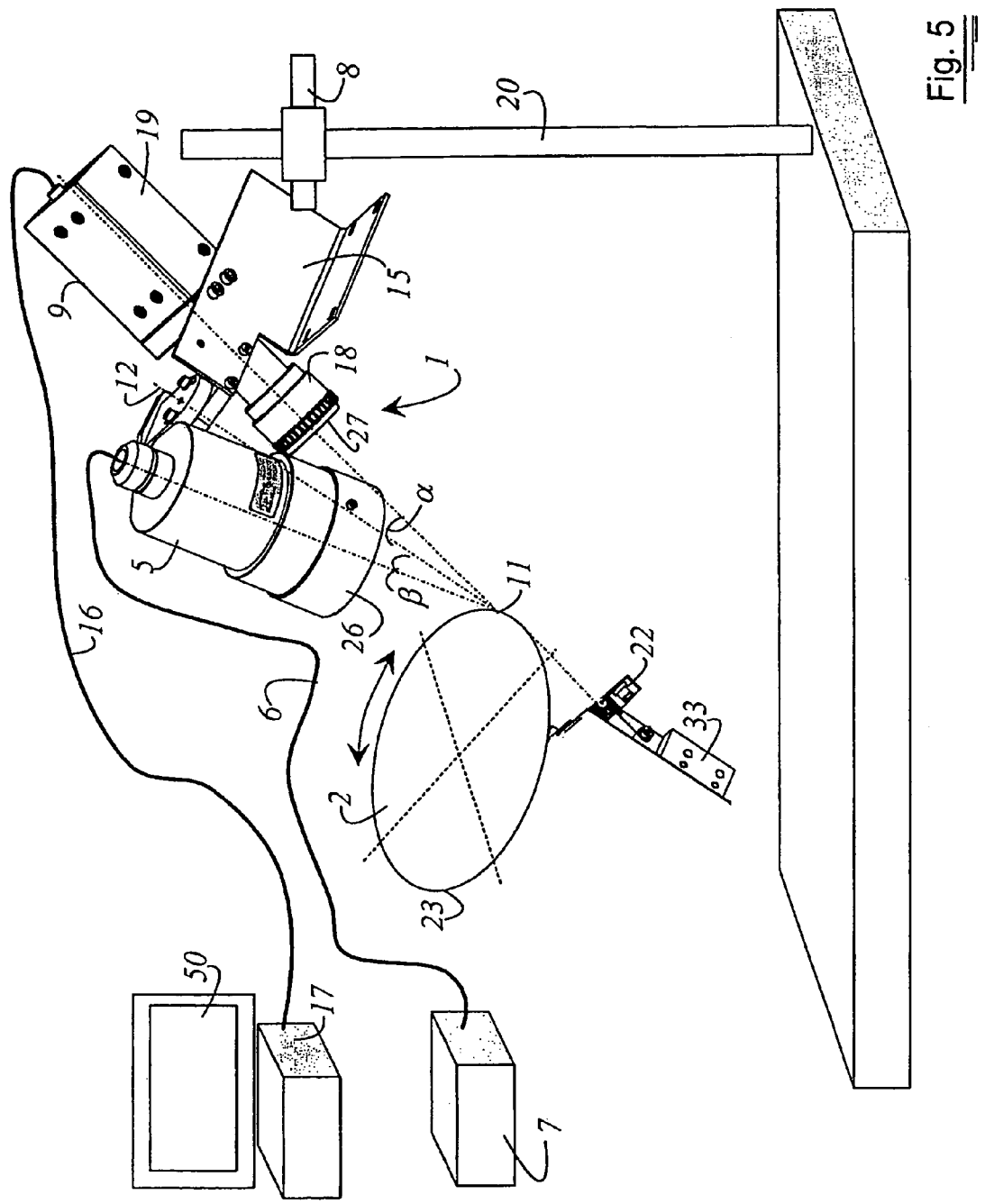
FIG. 5 is a perspective view of the apparatus according to FIG. 1.

FIG. 5 is a perspective view of the apparatus for wafer inspection shown in FIG. 1. Incident-light illumination device 5 and imaging device 9 are directed onto a region to be inspected of wafer 2 in the region of wafer edge 23. Wafer underside illumination device 22 illuminates wafer 2 from below. The light shining beyond wafer edge 23 is sensed by imaging device 9 so that in the image that is generated, the outline of wafer edge 23 appears as a salient light/dark transition.

For inspection of the entire wafer edge 23, wafer 2 is rotated about its vertical axis by rotation of receiving device 3. During a 360-degree rotation, data readout device 17, for example a computer with a frame grabber, reads out the linear camera several times, e.g. at regular intervals. The image data are then evaluated with special software, and from them the location of the photoresist edge with respect to wafer edge 23, and the location of regions from which resist has removed insufficiently or not at all, is respectively determined. The location of the wafer flat or the wafer notch can also be determined using the same method. A graphic depiction of wafer edge 23 on a display 50 associated with the computer is likewise possible.

For inspection of the wafer edge, it proves to be advantageous if a linear camera is used as camera 19, and if an LED row with an attached Fresnel lens (not depicted) is used as wafer underside illumination device 22. By precise alignment of the LED row beneath wafer 2, it is possible to image it directly and in precise alignment onto the linear array of linear camera 19.

A wide variety of objectives 18, both telecentric and non-telecentric objectives, can be used in combination with camera 19. An example of a non-telecentric objective is the Rodagon® 1:4/60 mm objective of the Rodenstock company, Germany, having a focal length F=60 mm, an objective field of approx. 0.028×57 mm, and a linear magnification M=1:2. An example of a telecentric objective is the Sill S5LPJ2005 objective of the Sill Optics company, Wandelstein, Germany.

A variety of application parameters can be optimized by selecting the objective and the linear magnification. Filters and stops (not depicted) are also, if applicable, to be inserted into the beam path in order to optimize the illumination.

The example described here of an apparatus for wafer inspection has an incident-light illumination device 5, a polychromatic cold light source with fiber optics, and a telecentric beam profile. An easily aligned construction results from the fact that illumination angle α is selected to be identical to image angle β. This is not necessary in principle, however, in order to produce good bright-field illumination of the region to be inspected on wafer 2, and slight differences between illumination angle α and image angle β are also possible.

As depicted in FIG. 5, support bar 15 is arranged on a displaceable support element 8 that is attached to a vertical part of stand 20. Support element 8 is horizontally displaceable so that the unit made up of incident-light illumination device 5 and imaging device 9 can be displaced together.

By horizontal displacement of support element 8, incidence point 11 (or the incidence region), and simultaneously the illumination region, can be positioned on any desired edge regions of wafer 3 that are to be inspected, and adapted to wafer diameters of different sizes. To make it easier to find desired edge regions to be inspected, wafer 2 can additionally be rotated about a vertical axis by means of rotatable receiving apparatus 3. The image data generated during inspection by the camera are transferred via a data line 16 into a data readout device 17, where they are available for further processing and evaluation in the computer.

To determine the quality of the edge region, the apparatus is aligned as described below, it being assumed that the quality of an edge-bead-removed region of wafer 2 is to be inspected. To perform an appropriate zero balancing as described above, incident-light illumination device 5 is first oriented in such a way that incidence point (incidence region) 11 is imaged exclusively onto regions of the wafer that are completely coated with a photoresist layer, i.e. are untreated. This zero balancing can be performed on a dummy, in which case the radial position of incidence point 11 requires no further modification later; or on a wafer 2 from which the edge bead has already been removed, for which purpose incidence point 11 must first be moved radially inward or to regions of wafer 2 completely coated with the photoresist layer. Provided for this purpose is a mechanism for relative displacement of wafer 2 and wafer inspection apparatus 1, which can be implemented, for example, by a translation device for displacing receiving device 3 and/or by a translation step for displacing wafer inspection apparatus 1 and/or by pivoting support bar 15 relative to the upright portions of stand 20.

Firstly, illumination angle α is selected appropriately. For this, incident-light illumination device 5 is displaced along alignment rail 24 for the α-adjustment (FIG. 4) until a suitable illumination angle α is found (as described below). In this position, the illuminating light strikes the surface of wafer 2 at incidence point 11. Imaging device 9 is then displaced, by pivoting along alignment rail 21 for the α-adjustment (FIG. 1), until bright-field illumination for apparatus 1 is achieved (angle of incidence=angle of reflection). In this position, illumination angle (α substantially corresponds to image angle β.

Polarizers 26 and 27 can be removed for this alignment. Then, if necessary, polarizers 26, 27 are placed onto incident-light illumination device 5 and imaging device 9 respectively, and the transmission axes are then, as described below, adjusted to a predetermined angle relative to one another.

The transmission axes of polarization filters 26 and 27 are preferably selected so that essentially no light is reflected into imaging device 9. The transmission axes are therefore usually oriented orthogonally to one another, i.e. polarizer 26 and polarizer 27 constitute a pair made up of a polarizer and a crossed analyzer. As shown in FIG. 5, illumination angle α can be comparatively small, e.g. in the range from approximately 10 degrees to approximately 20 degrees, preferably being in the range from approximately 14 degrees to approximately 16 degrees, and even more preferably approximately 15 degrees. In this angular position, in particular even features protruding vertically from surface 42 of wafer 2, and their sides, are imaged into imaging device 9, so that resist removal from side wall segments can also be assessed.

In principle, however, any illumination angle α up to raking incidence, i.e. up to approximately α=90°, can be selected; this also depends on the features applied to wafer 2.

According to a further preferred embodiment, the illumination angle α is selected so that it corresponds substantially to the Brewster angle of the material of wafer 2 to be inspected, or of a layer, in particular a photoresist layer, applied onto wafer 2 to be inspected. In this configuration, the light reflected from surface 42 of wafer 2 is polarized substantially completely perpendicular to the image plane, even if the illuminating light itself is not polarized. The aforementioned Brewster angle can be calculated in known fashion from the refractive index of the material of wafer 2 or of the material of the applied layer, in particular the photoresist layer, and set as the illumination angle α. The polarization of the reflected beam under the Brewster condition can also be used for appropriate orientation of the transmission axes of polarizers 26 and 27. The transmission axis of polarizer 26 is preferably oriented substantially perpendicular to the image plane, whereas the transmission axis of polarizer 27 is oriented substantially perpendicular to that of polarizer 26, i.e. lies substantially in the image plane. In this position the illumination angle α can also be realigned further in order to meet the Brewster condition even better or to optimize a zero balance. In this position, ideally no light should be reflected back into imaging device 9. Because of inhomogeneities and irregularities on surface 42 of wafer 2, however, it may happen that the zero balance cannot be performed completely. In any case, in this position a minimal intensity is still reflected back into imaging device 9.

Incidence point 11 is then displaced onto a region that is to be inspected, where both untreated regions (i.e. regions that are completely coated with a photoresist layer) and treated regions (i.e. regions from which resist has been substantially completely removed) are present. This relative displacement of wafer 2 and wafer inspection apparatus 1 can be brought about in the manner mentioned above.

The polarization state of the light, upon reflection at the treated regions of the surface region to be inspected, for example in edge-bead-removed region 23 of wafer 2, is influenced differently than at untreated surface regions. A rotation of the polarization direction of the reflected light thus occurs, so that a portion of that light travels into imaging device 9 and is detected there. Because of the high gain that can be selected according to the present invention, the treated regions, in particular edge-bead-removed wafer regions, can be imaged and displayed better according to the present invention.

The apparatus according to the present invention for wafer inspection can be integrated into the production process as a separate inspection unit. It is also conceivable, however, to integrate the apparatus according to the present invention into an already existing wafer inspection system. This is done, for example, by providing in the apparatus an automated handling device for semi-automatic or automatic placement and subsequent removal of wafers 2 to be inspected.

Because wafer 2 can be rotated about a normal line as depicted in FIG. 5, it is also possible with wafer inspection system 1 according to the present invention to perform a spatially resolved detection of incompletely edge-bead-removed regions on surface 42 of wafer 2. With a knowledge of the circumferential zero position of wafer 2—which can be determined by detection of the wafer notch or the wafer flat or another marking, as described below with reference to FIG. 6 the circumferential position of the completely edge-bead-removed regions can be spatially resolved. Wafer 2 can of course also be displaced in any desired manner parallel to its surface 42 by means of the translation step described previously, so that regions located radially inward can also be inspected.

The aforesaid binary decision can be used to pick out wafers that have been found to have incomplete edge bead removal, so that the applied photoresist can be rinsed or dissolved off again and the corresponding process steps can be performed once again, until a complete or at least satisfactory edge bead removal is ascertained.

Figure 6:
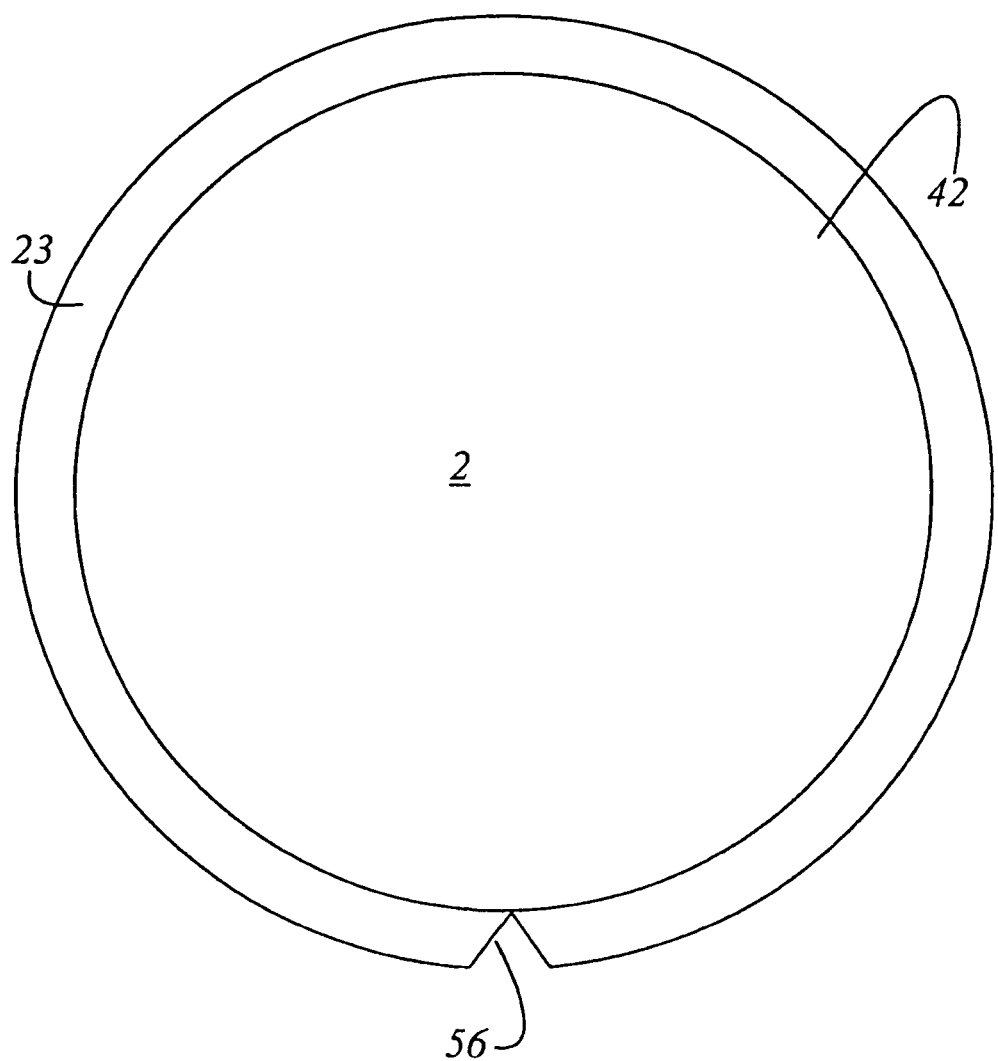
FIG. 6 is a schematic plan view of a wafer to be inspected.

FIG. 6 is a schematic plan view of a wafer 2 to be inspected. Wafer 2 is coated over substantially its entire surface with a photoresist (not depicted). The photoresist has been substantially completely removed from a region of the overall wafer edge 23, for example by selective spraying of a solvent in the region of wafer 23 and possible subsequent light exposure. Wafer 2 has on wafer edge 23 a notch 56 or at least a flat (not depicted). The flat or notch 56 serves to define the angular position of wafer 2.

The angular position of wafer 2 is defined as follows: As indicated by rotation arrow 46 in FIG. 1, wafer 2 is mounted rotatably on receiving device 3. As described previously, in order to image edge region 23 of wafer 2, wafer underside illumination device 22 is aligned in such a way that a portion of the light emitted by it is imaged into imaging device 9. When notch 56 arrives in the beam path of the light emitted by wafer underside illumination device 22 upon rotation of wafer 2, that light is imaged in imaging device 9. The corresponding angular position pertaining thereto can be used as a reference for the circumferential zero position.

What is claimed is:

1. An apparatus for wafer inspection, comprising an incident-light illumination device having an illumination axis, an imaging device having an image axis, wherein both the illumination axis and the image axis are inclined with respect to one another and are directed onto a region on a surface of a wafer to be inspected, and a polarizing device is associated with each of the incident-light illumination device and the imaging device, wherein transmission axes of the polarizing devices are oriented at a predetermined angle to one another,
wherein the region to be inspected is located on a wafer edge; and a wafer underside illumination device, which illuminates the imaging device from below beyond the wafer edge, is additionally arranged below the wafer edge.

2. The apparatus as defined in claim 1, wherein the transmission axes of the two polarizing devices are substantially perpendicular to one another.

3. The apparatus as defined in claim 1, wherein the illumination axis and the image axis intersect at an incidence point of the image axis on the wafer.

4. The apparatus as defined in claim 3, wherein the illumination axis is inclined at an illumination angle α>0 with respect to a wafer normal line through the incidence point.

5. The apparatus as defined in claim 4, wherein the inclination of the image axis with respect to the wafer normal line is defined by the incidence point of an image angle β; and the image angle is equal to the illumination angle α.

6. The apparatus as defined in claim 4, wherein the illumination angle α corresponds to the Brewster angle of the material of the wafer to be inspected or of a layer applied onto the wafer to be inspected.

7. The apparatus as defined in claim 4, wherein the illumination angle α is in the range from approximately 10° to approximately 20°.

8. The apparatus as defined in claim 4, wherein the illumination angle α and/or an image angle β is modifiable.

9. The apparatus as defined in claim 1, wherein the illumination device comprises a polychromatic light source.

10. The apparatus as defined in claim 1, wherein the illumination device comprises a monochromatic light source.

11. The apparatus as defined in claim 1, wherein the imaging device comprises an objective and a camera.

12. The apparatus as defined in claim 11, wherein there is associated with the camera a data readout device that sequentially reads out image data of the camera during rotary motion of the wafer; and the data readout device is also associated with a computer that controls the data readout device.

13. The apparatus as defined in claim 12, wherein after a rotation of the wafer through at least 360°, the data readout device together with the computer determines, from the sequentially acquired image data, a quality and/or extent or position of an edge of an edge-bead-removed region (EBR) relative to the wafer edge.

14. The apparatus as defined in claim 13, wherein the data readout device, together with the computer, determines from the sequentially acquired image data the position of a notch or a flat on the wafer edge.

15. The apparatus as defined in claim 1, wherein the imaging device comprises an objective and a linear camera.

16. The apparatus as defined in claim 1, wherein a receiving device that is rotatable about its vertical axis is provided for placement of the wafer.

17. The apparatus as defined in claim 16, wherein a motorized drive system for rotating the receiving device is associated with the receiving device.

18. An apparatus for wafer inspection, comprising an incident-light illumination device having an illumination axis, an imaging device having an image axis, wherein the illumination axis and the image axis are inclined with respect to one another and are directed onto a region on a surface of a wafer, wherein the region to be inspected is located on a wafer edge, a polarizing device associated with each of the incident-light illumination device and the imaging device, wherein transmission axes of the polarizing devices are oriented at a predetermined angle to one another, and a wafer underside illumination device is arranged below the wafer edge, which illuminates the imaging device from below beyond the wafer edge.

19. An apparatus for wafer inspection, comprising an incident-light illumination device having an illumination axis, an imaging device having an image axis, wherein the illumination axis and the image axis are inclined with respect to one another and are directed onto a region on a surface of a wafer, wherein the region to be inspected is located on a wafer edge, a polarizing device associated with each of the incident-light illumination device and the imaging device, wherein transmission axes of the polarizing devices are oriented at a predetermined angle to one another, a wafer underside illumination device is arranged below the wafer edge, which illuminates the imaging device from below beyond the wafer edge, a receiving device rotatable about its vertical axis is provided for placement of the wafer; a motorized drive system that rotates the receiving device is associated with the receiving device, and a data readout device being associated with a camera, wherein the data readout device sequentially reads out the image data of the camera during the rotary motion of the wafer; and the data readout device is also associated with a computer that controls the data readout device.

20. The apparatus as defined in claim 7, wherein the illumination angle $\alpha$ is in the range from approximately 14° to approximately 16°.

21. The apparatus as defined in claim 7, wherein the illumination angle $\alpha$ is approximately 15°.

* * * * *